(12) United States Patent
Mihalko et al.

(10) Patent No.: US 8,491,662 B2
(45) Date of Patent: Jul. 23, 2013

(54) KNEE PROSTHESIS

(75) Inventors: William Mihalko, Germantown, TN (US); Khaled J. Saleh, Springfield, IL (US); Saïd Moussa, Chamarandes (FR); Dominique Mouillet, Semoutiers (FR)

(73) Assignee: Aesculap AG, Tuttlingen (DE)

( * ) Notice: Subject to any disclaimer, the term of this patent is extended or adjusted under 35 U.S.C. 154(b) by 83 days.

(21) Appl. No.: 13/291,209

(22) Filed: Nov. 8, 2011

(65) Prior Publication Data

US 2012/0143342 A1 Jun. 7, 2012

Related U.S. Application Data

(63) Continuation-in-part of application No. 12/484,594, filed on Jun. 15, 2009, now abandoned.

(60) Provisional application No. 61/140,183, filed on Dec. 23, 2008.

(51) Int. Cl.
*A61F 2/38* (2006.01)

(52) U.S. Cl.
USPC .................................. 623/20.27; 623/20.21

(58) Field of Classification Search
CPC ....................................................... A61F 2/38
USPC .......................................... 623/20.21–20.27
See application file for complete search history.

(56) References Cited

U.S. PATENT DOCUMENTS

| 4,209,861 A | 7/1980 | Walker et al. |
| 4,213,209 A | 7/1980 | Insall et al. |
| 4,298,992 A | 11/1981 | Burstein et al. |
| 5,007,933 A | 4/1991 | Sidebotham et al. |
| 5,147,405 A | 9/1992 | Van Zile et al. |
| 5,236,461 A | 8/1993 | Forte |
| 5,549,686 A | 8/1996 | Johnson et al. |
| 5,702,458 A | 12/1997 | Burstein et al. |

(Continued)

FOREIGN PATENT DOCUMENTS

| DE | 31 01 789 | 1/1991 |
| DE | 690 09 509 | 9/1994 |

(Continued)

OTHER PUBLICATIONS

Blaha, J. David, M.D., The Rationale for a Total Knee Implant That Confers Anteroposterior Stability Throughout Range of Motion, The Journal of Arthroplasty, vol. 19, No. 4, Suppl. 1 2004, Elsevier, Inc. 2004, USA.

(Continued)

*Primary Examiner* — Jason-Dennis Stewart
(74) *Attorney, Agent, or Firm* — RatnerPrestia

(57) ABSTRACT

A knee prosthesis includes a femoral component having two condyles and an asymmetrical cam extending between the condyles. The cam has a medial end and a lateral end. The knee prosthesis also includes a tibial component having bearing surfaces and a post disposed between the bearing surfaces. The femoral component and tibial component are engageable by contact between the femoral condyles and tibial bearing surfaces, and by contact between the cam and post. The cam includes a first curvature defined by a first plane passing through the cam, and a second curvature defined by a second plane passing through the cam, the first curvature having a first vertex, and the second curvature having a second vertex, the distance between the first vertex and a medial plane being greater than the distance between the second vertex and the medial plane.

14 Claims, 17 Drawing Sheets

U.S. PATENT DOCUMENTS

| | | | |
|---|---|---|---|
| 5,906,643 | A | 5/1999 | Walker |
| 5,964,808 | A | 10/1999 | Blaha et al. |
| 6,013,103 | A | 1/2000 | Kaufman et al. |
| 6,080,195 | A | 6/2000 | Colleran et al. |
| 6,206,926 | B1 | 3/2001 | Pappas |
| 6,325,828 | B1 | 12/2001 | Dennis et al. |
| 6,443,991 | B1 | 9/2002 | Running |
| 6,558,426 | B1 | 5/2003 | Masini |
| 6,726,723 | B2 | 4/2004 | Running |
| 7,160,330 | B2 | 1/2007 | Axelson, Jr. et al. |
| 7,326,252 | B2 | 2/2008 | Otto et al. |
| 7,413,577 | B1 | 8/2008 | Servidio |
| 7,678,152 | B2 | 3/2010 | Suguro et al. |
| 7,981,159 | B2 | 7/2011 | Williams et al. |
| 2004/0243244 | A1 | 12/2004 | Otto |
| 2004/0243245 | A1 | 12/2004 | Plumet et al. |
| 2005/0192672 | A1 | 9/2005 | Wyss et al. |
| 2006/0136066 | A1 | 6/2006 | Plumet et al. |
| 2007/0135925 | A1 | 6/2007 | Walker |
| 2008/0097615 | A1 | 4/2008 | Lipman et al. |
| 2008/0119940 | A1 | 5/2008 | Otto et al. |
| 2009/0306785 | A1 | 12/2009 | Farrar et al. |
| 2009/0319048 | A1 | 12/2009 | Shah et al. |
| 2010/0016979 | A1 | 1/2010 | Wyss |
| 2010/0161067 | A1 | 6/2010 | Saleh |

FOREIGN PATENT DOCUMENTS

| | | |
|---|---|---|
| DE | 692 04 201 | 1/1996 |
| DE | 699 06 035 | 1/2004 |
| DE | 695 32 047 | 6/2004 |
| DE | 602 16 157 | 9/2007 |
| DE | 20 2009 012 704 | 12/2009 |
| EP | 0381352 | 8/1990 |
| EP | 0510299 | 10/1992 |
| EP | 0941719 | 9/1999 |
| EP | 1050283 | 11/2000 |
| EP | 1591082 | 11/2005 |
| GB | 2067412 | 7/1981 |
| GB | 2253147 | 9/1992 |
| WO | WO 2004 058108 | 7/2004 |
| WO | WO 2007 119173 | 10/2007 |
| WO | WO-2009-105495 A1 | 8/2009 |
| WO | WO-2009105495 A1 | 8/2009 |
| WO | WO 2010/075365 | 12/2009 |
| WO | WO-2010108550 A1 | 9/2010 |

OTHER PUBLICATIONS

Chandran, Nagarajan, et al., Optimisation of the Posterior Stabilised Tibial Post for Greater Femoral Rollback After Total Knee Arthroplasty—A Finite Element Analysis, International Oprthopedics (SICOT) (2009); vol. 33; pp. 687-693; Springer-Verlag 2008.

Churchill, D. L., Ph.D., et al.; The Influence of Femoral Rollback on Patellofemoral Contact Loads in Total Knee Arthroplasty; The Journal for Arthroplasty; vol. 16, No. 7, 2001; pp. 909-918.

Kochmond, Jonathan H., M.S. et al.; Stability and Range of Motion of Insall-Burstein Condylar Protheses: A Computer Simulation Study; The Journal for Arthroplasty; vol. 10, No. 3, 1995; pp. 383-388.

Suggs, Jeremy F. et al.; Patient Function After a Posterior Stabilizing Total Knee Arthroplasty: Cam-Post Engagement and Knee Kinematics; Knee Surg Sports Traumatol Arthrosc (2008); vol. 16; pp. 290-296; Springer-Verlag 2007.

Tamaki, Masashi, M.D., et al.; In Vivo Kinematic Analysis of a High-Flexion Posterior Stabilized Fixed-Bearing Knee Prosthesis in Deep Knee-Bending Motion; The Journal of Arthroscopy; vol. 23, No. 6, 2008; pp. 879-885; Elsevier, Inc. 2008.

Walker, Peter S., Ph.D.; Design Features of Total Knees for Achieving Normal Knee Motion Characteristics; The Journal of Arthroscopy; vol. 24, No. 3; 2009; pp. 475-483; Elsevier, Inc. 2009.

Mihalko, William M., PhD. and Krackow, Kenneth A., M.D.; Posterior Cruciate Ligament Effects on the Flexion Space in total Knee Arthroplasty; Clinical Orthopaedics and Related Research; Jul. 30, 1997; pp. 243-250; No. 360; Lippencott Williams & Wilkins, Inc.; 1999.

International Search Report for PCT/US2009/069163, mailed Jul. 5, 2010.

U.S. Patent and Trademark Office Non-Final Office Action for U.S. Appl. No. 12/484,594 Dated Mar. 21, 2011.

U.S. Appl. No. 13/141,569, filed Dec. 14, 2011, Khaled Saleh et al. (U.S. National Phase Application of PCT/US2009/069163 cited on PTO/SB08a form, p. 2).

U.S. Patent and Trademark Office Non-Final Office Action for U.S. Appl. No. 12/484,594 Dated Dec. 22, 2010.

U.S. Patent and Trademark Office Non-Final Office Action for U.S. Appl. No. 12/484,594 Dated Mar. 26, 2010.

International Application Serial No. PCT/IB2012/002240, International Search Report and Written Opinion mailed Jan. 2, 2013, 6 pgs.

KNEE PROSTHESIS

CROSS REFERENCE TO RELATED APPLICATIONS

This application is a continuation-in-part of U.S. application Ser. No. 12/484,594, filed Jun. 15, 2009, which claims the benefit of U.S. Provisional Application Ser. No. 61/140,183, filed Dec. 23, 2008. The contents of both applications are incorporated by reference herein.

FIELD

The field of invention relates to artificial joints, and more particularly to knee prostheses.

BACKGROUND

As is the case with many joint prostheses or replacements, replicating natural anatomical movement through artificial mechanical devices proves challenging. This is true especially with the knee, which allows for relative complex movement and kinematics between the femoral condyles and the tibia. This relative motion is complex in that it accounts for both rolling and sliding between the contact surfaces at varying rates throughout the flexion arc. Along with such movement during knee bending is a rotational movement between the tibia and femur. As such, knee prostheses have historically tried to replicate the full range of knee movement, throughout and between full flexion and extension in all planes (coronal-varus/valgus, sagittal-flexion, transverse-rotation). True anatomical movement would allow rollback and translation of the femoral condyles on the tibia, all while also allowing rotational movement during flexion/extension.

Prior art designs have included femoral components with cams and tibial components with posts. It has been disclosed that an asymmetrical cam can be utilized to cause rotation between the two components. These designs, however, have taught architectures that require relatively high posts to support upward movement of the cam during flexion.

SUMMARY

The drawbacks of known femoral and tibial components are resolved in many respects by knee prostheses in accordance with the invention. In one embodiment, a knee prosthesis includes a femoral component having two condyles with an opening disposed between the two condyles, and an asymmetrical cam extending between the condyles. The cam includes a medial end generally conforming to a medial plane, a lateral end generally conforming to a lateral plane that extends generally parallel to the medial plane, a longitudinal axis extending from the medial end to the lateral end generally perpendicularly to the medial and lateral planes, and a central plane that extends generally parallel to and equidistant from the medial plane and lateral plane. The knee prosthesis also includes a tibial component having bearing surfaces to support each of the femoral component condyles, and a post disposed between the bearing surfaces and extending superiorly from the tibial component.

The femoral component and tibial component may be engageable by contact between the femoral condyles and tibial bearing surfaces, and by contact between the cam and post, during at least a portion of flexion between the femoral and tibial components. The cam may include a first curvature defined by a first plane passing through the cam, and a second curvature defined by a second plane passing through the cam, the first and second planes each extending generally parallel to the longitudinal axis and perpendicular to the central plane.

The cam and post may be configured so that the first curvature on the cam contacts the post at a lower degree of flexion, and the second curvature on the cam contacts the post at a higher degree of flexion. The lower degree of flexion may be a flexion of about 45° and the higher degree of flexion may be a flexion of about 145°. The first curvature may include a concave curve having a first vertex, and the second curvature may include a concave curve having a second vertex. The distance between the medial plane and the first vertex may be greater than the distance between the medial plane and the second vertex, such that moving the femoral and tibial components in flexion from the lower degree of flexion to the higher degree of flexion causes the femoral component to rotate about the post.

The concave curve of the first curvature may be substantially symmetrical with respect to the central plane, and the concave curve of the second curvature may be asymmetrical with respect to the central plane. The cam may be comprised of a plurality of curvatures between the first and second curvatures. Each of the plurality of curvatures may include a concave curve with a vertex. The distance between the medial plane and the vertex of each curve may gradually decrease from the first curvature toward the second curvature.

The cam may form a posterior boundary of the opening between the condyles. The posterior boundary may form a U-shaped curve that is symmetrical with respect to the central plane. The post may include an inclined contact surface having a U-shaped curvature that mates with the U-shaped curve of the posterior boundary of the opening during at least a portion of flexion between the femoral and tibial components.

The lateral end of the cam may have a larger cross-sectional area than the medial end of the cam. In addition, the lateral end may include a lobe region having a convex curvature. The cam may include a first surface between the medial and lateral ends having a uniform contour and a second surface between the medial and lateral ends having a non-uniform contour. The first and second surfaces may border one another along a ridgeline that extends between the first and second surfaces. The ridgeline may extend from the medial end to the lateral end. The ridgeline may follow a U-shaped curve between the medial end and the lateral end. The U-shaped curve may have a vertex. The distance between the vertex of the ridgeline and the lateral plane may be greater than the distance between the vertex of the ridgeline and the medial plane.

DETAILED DESCRIPTION

Figure 1:
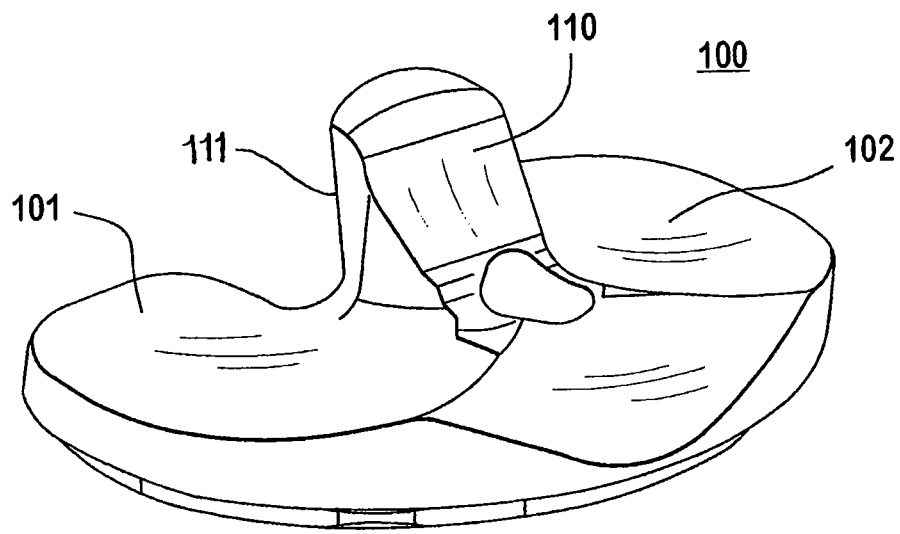
FIG. 1 illustrates a tibial component in accordance with the present invention.

Although the invention is illustrated and described herein with reference to specific embodiments, the invention is not intended to be limited to the details shown. Rather, various modifications may be made in the details within the scope and range of equivalents of the claims and without departing from the invention.

The present invention provides a knee prosthesis which allows for anatomically correct knee movement. It does so by providing an upper, or femoral, component which is designed to mechanically interact with a lower, or tibial, component to achieve kinematic movement consistent with a natural knee joint. Generally, the two pieces interact by providing several different contact surfaces, not all of which are engaged between the two components of the knee throughout the range of motion.

Two such contact surfaces are the load bearing condylar surfaces between the femoral component and the tibial component. These surfaces are defined by medial and lateral condylar surfaces which are referred to as the load bearing surfaces for a given knee joint. Specifically, a medial load bearing surface is defined between the medial femoral condyle and its counterpart on the tibial component, namely a medial tibial accommodating surface. Likewise, a lateral load bearing surface is defined between the lateral femoral condyle and its counterpart on the tibial component, namely a lateral tibial accommodating surface.

A different contact surface also exists, however, to cause rotational movement between the femoral and tibial components, during certain degrees of knee extension/flexion which will allow for a kinematic pattern that more closely resembles that of the natural knee. This contact surface is defined by interaction between a post on the tibial component (preferably polyethylene) and a cam surface on the femoral component (preferably metallic). Because the point of contact between the femoral condyles and their corresponding tibial load-receiving components changes in an anterior/posterior direction (that is to say there is front/back translation of the point of contact) during knee movement, the post and cam do not interact during all degrees of knee flexion. Instead, the post and cam only interact during those points of knee movement for which they are designed to cause a replicated natural knee kinematic envelop. This interaction occurs when the anterior/posterior movement of the femoral/tibial contact causes the post and cam to engage, or when flexion of the knee causes enough rollback of the femoral component to engage the tibial post against the cam of the femoral component.

It should be noted, however, that once flexion typically reaches about 45°, anterior/posterior translation does not stop but occurs at different rates in the medial and lateral compartments of the knee. Moreover, as the knee bends, the lateral condyle rolls back to a position of about 10-15 mm posterior at about 120° flexion, but the medial condyle rolls back only about 4-5 mm to a final position of about 1-3 mm posterior. This difference in posterior movement in the two compartments of the knee is seen as rotation of the femoral component on the tibial component, and occurs with continued rollback of the femoral condyles. This interaction of the post and cam, as well as the movement of the femoral condyles with respect to the tibial bearing surfaces will be addressed below.

The movement described is achieved through the present invention's architecture of the both the femoral component, the tibial component, and in particular the cam and post dimensions. All of these aspects are integrated into a system which provides for sophisticated, anatomical movement within the prosthetic knee of the present invention.

FIG. 1 shows a tibial component 100 in accordance with the present invention. This tibial component 100 has two load bearing surfaces, shown as load bearing surface 101 and load bearing surface 102. For a right knee joint, load bearing surface 101 would be the lateral condyle load bearing surface, and load bearing surface 102 would be the medial condyle load bearing surface. Post 110 is shown extending upward, or in a superior direction, from the lateral plane generally defining the tibial insert. Post 110 will be described in more detail below.

Figure 2:
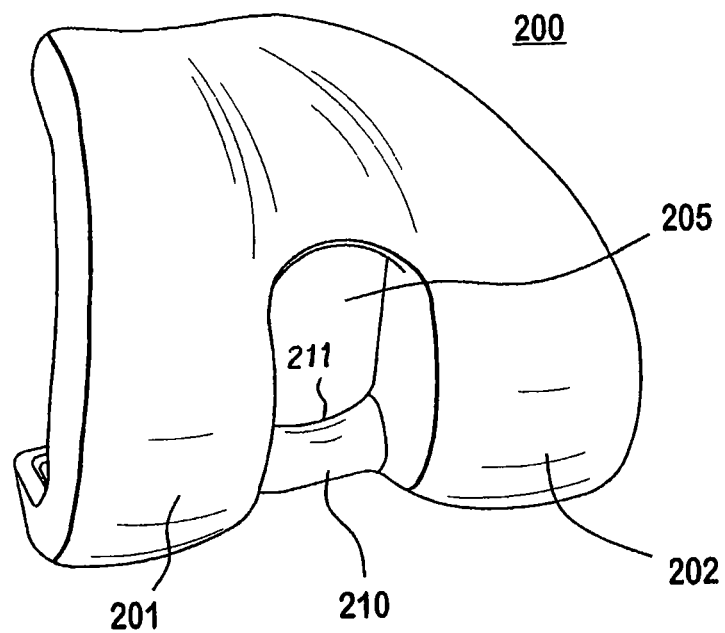
FIG. 2 illustrates a femoral component in accordance with the present invention.

FIG. 2 illustrates a femoral component 200 in accordance with the present invention. Cam 210 is shown bridging a gap between the femoral condyles 201 and 202. Opening 205 is defined by the condyles 201 and 202 which extend anteriorly around the side of the opening opposite cam 210. Cam 210 is generally disposed in a posterior portion of the opening 205 in the femoral component, wherein the cam forms a posterior boundary 211 of the opening. Posterior boundary 211 forms a U-shaped curve that is symmetrical. Post 110 comprises an inclined contact surface 111. Inclined contact surface 111 has a U-shaped curvature that mates with the U-shaped curve of posterior boundary 211 of opening 205 during at least a portion of flexion between the femoral and tibial components. As will be described, inclined contact surface 111 causes cam 210 to move inferiorly relative to post 110 as the femoral and tibial components move from a lower degree of flexion to a higher degree of flexion.

Figure 3:
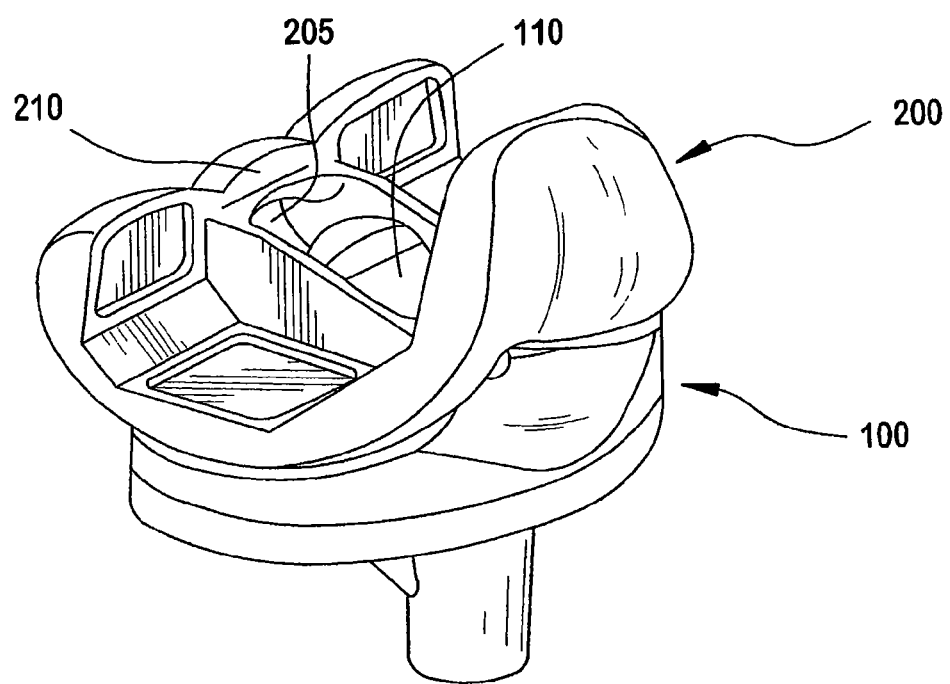
FIG. 3 illustrates a tibial component (with a stem) and a femoral component mated in accordance with the present invention.
Figure 4:
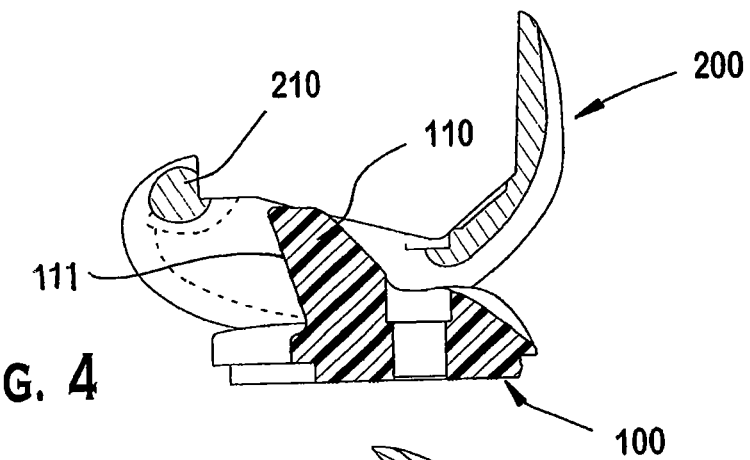
FIG. 4 illustrates a partial cross sectional view of the prosthesis of the present invention at about 0° flexion.

FIG. 3 shows femoral component 200 disposed atop tibial component 100. Post 110 is shown extending through opening 205. FIG. 3 shows the components in a position of 0° flexion. As can be seen from FIG. 3, cam 210 is not in contact with post 110 at this point. It is also noteworthy that in this position, there is no contact between the anterior surface of post 110 and the anterior boundary of opening 205. This aspect can be seen perhaps more clearly in FIG. 4, which shows a partial cross sectional view of that shown in FIG. 3. This aspect of the present invention is important because it reduces wear on the tibial post 110.

For an example of an implant having both anterior and posterior cams, see U.S. Pat. No. 6,325,828, which illustrates a femoral component having a blind hole or slot/recess (as opposed to an opening) bordered by cams on both sides (anterior and posterior). As such, and as explicitly disclosed, the anterior cam engages the post at full extension (or 0° flexion).

Figure 5:
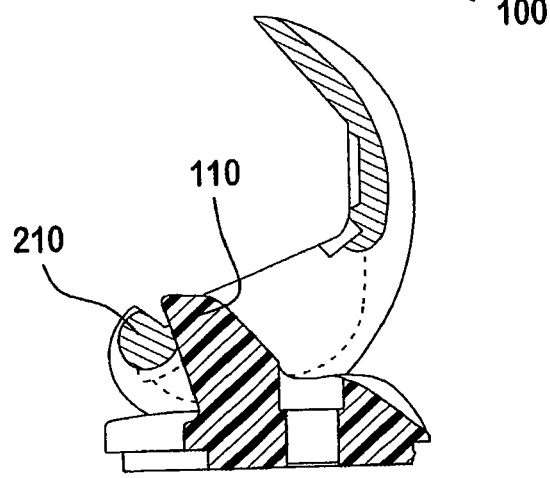
FIG. 5 illustrates a partial cross sectional view of the prosthesis of the present invention at about 90° flexion.

As the knee bends toward a flexion of about 45°, cam 210 moves toward post 110 as anterior translation occurs between the contact region of the femoral condyles and their respective load bearing surfaces on tibial component 100. The orientation of the two components, and in particular the cam and post, at 45° flexion, is illustrated in FIG. 5, which shows a partial cross sectional view of the components at about 45° flexion. At this point in the knee movement, the cam 210 has contacted post 110 and as further flexion occurs, the rotational movement caused by the interaction of the post and cam causes slight medial rotation of the femoral component with respect to the tibial component.

Figure 6:
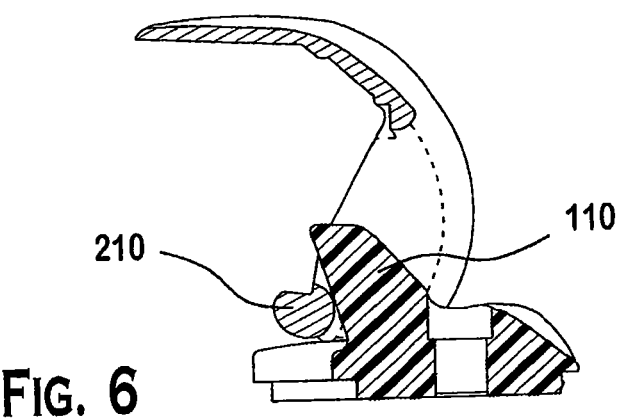
FIG. 6 illustrates a partial cross sectional view of the prosthesis of the present invention at about 145° flexion.

FIG. 6 shows the partial cross section of the two components after further knee flexion. Note that the contact point between the cam and post moves downward along the post, or inferiorly, as flexion increases. This is due to the architecture of the cam and post and is designed as a part of the knee movement based on the anatomical requirements of the natural knee joint.

Figure 7:
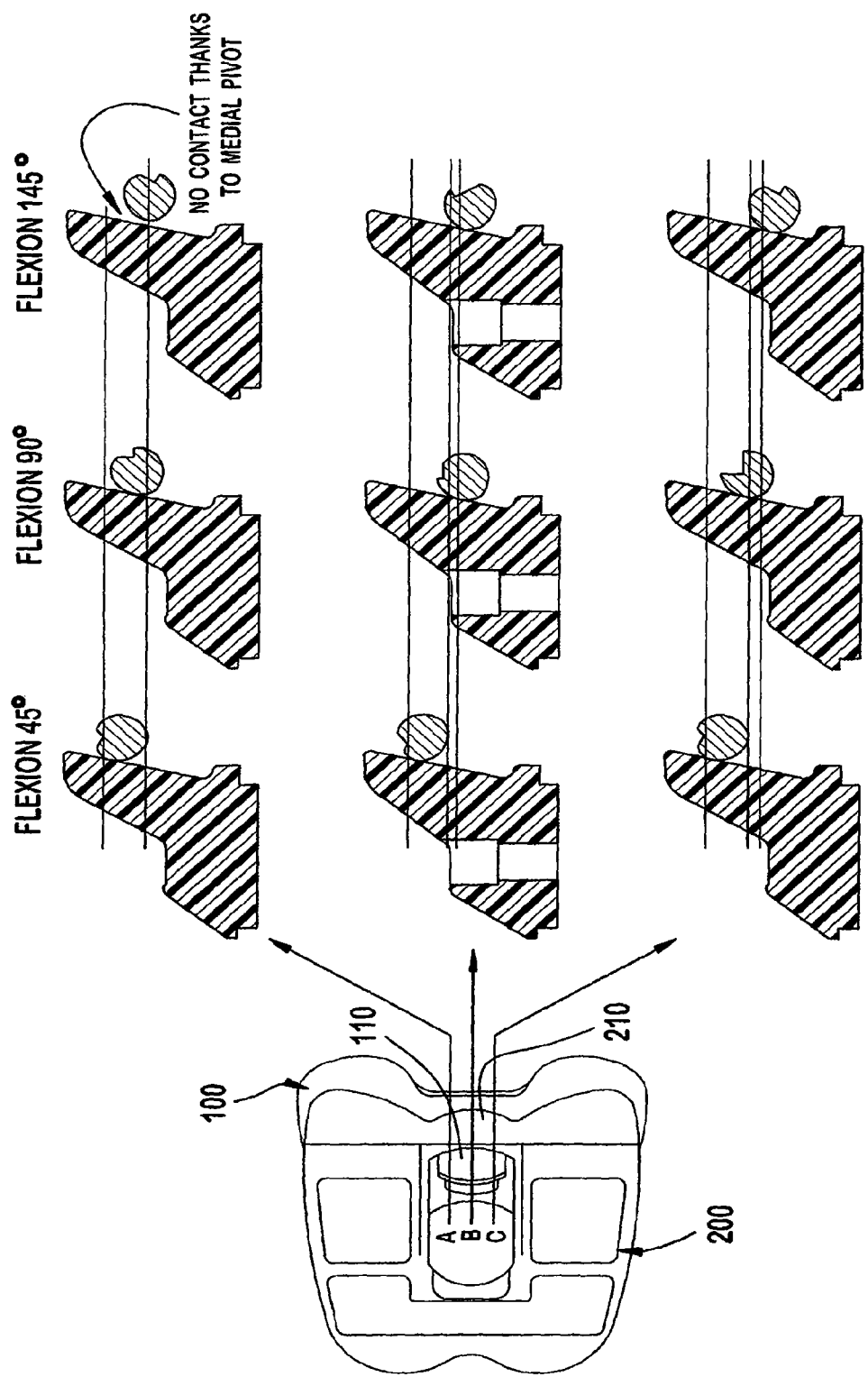
FIG. 7 illustrates a series of cross sectional views at three planes of interaction of the cam and post in accordance with the present invention.

Further defining this aspect of the invention is FIG. 7. FIG. 7 shows the cross sections of three different planes at three different angles of flexion. Planes A, B, and C are shown and illustrate the asymmetry of the cam 210 and the effect of that asymmetry on the rotation and inferior movement of the cam down the post as flexion increases. At 45° flexion, plane A indicates contact of the cam and post at a point relatively high on the post. As flexion increases to 90°, the cam is working its way down the post as the femoral component rotates medially with respect to the tibial component. At 145° flexion, not only has the cam moved further downward along the posterior side of the post (at planes B and C), but in fact, at plane A, or the lateral side of the cam, the cam has disengaged the post altogether as medial rotation has separated the cam from the post at this point. Thus, there is seen a medial rotation consistent with natural knee movement while the cam has actually moved down along the post. Stability is one advantage of the implant designed this way in accordance with the invention.

Figure 8:
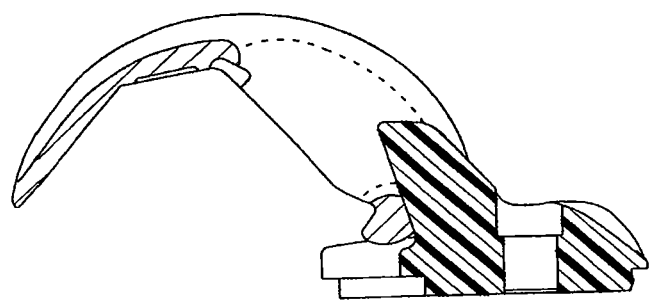
FIG. 8 illustrates a partial cross sectional view of the prosthesis of the present invention at about full flexion.

This later point is important to achieve natural knee movement with respect to a patellar implant. FIG. 8 shows knee prosthesis of the present invention at about 145° flexion. At this point, and as noted above, the cam has moved downward along the post. The post therefore only needs to be as high as is necessary to engage the cam at the first point of contact, namely at about 45° flexion (because after that the cam moves downward).

Figure 9:
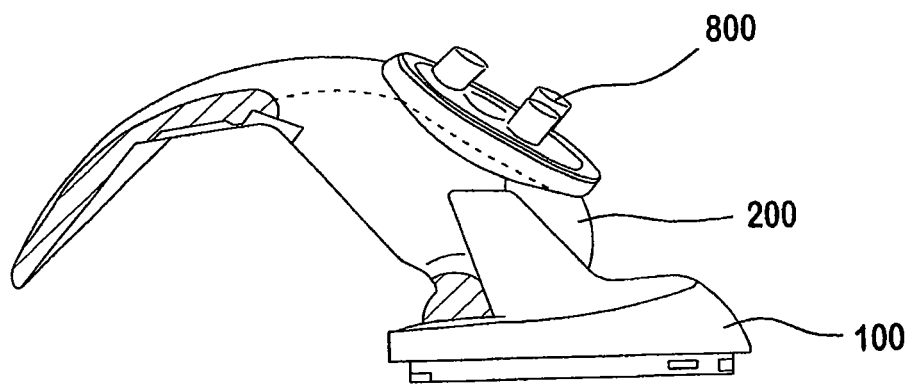
FIG. 9 illustrates that of FIG. 8 but with the addition of a patellar implant.

The relative shortness of the post is important because it allows for clearance of the patellar implant as shown in FIG. 9. There, patellar implant 800 is shown disposed on femoral component 200. Unlike prior art designs that have upward cam movement during flexion, and therefore require higher posts to extend upward from the initial point of contact, the present invention is configured to provide downward cam movement and therefore relatively shorter posts are necessary. This allows for patellar clearance during knee rotation as shown in FIG. 9.

Figure 10:
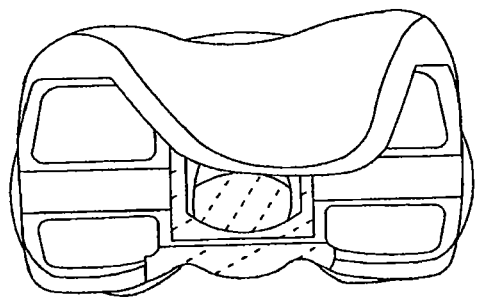
FIG. 10 illustrates a top down view of the prosthesis of the present invention at about 45° flexion.
Figure 11:
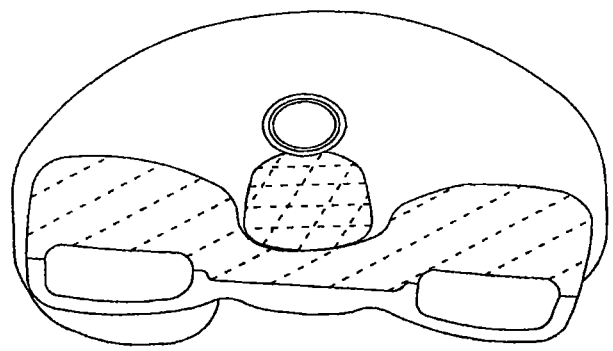
FIG. 11 illustrates a partial cross sectional view from the top down of the prosthesis of the present invention at about 90° flexion.
Figure 12:
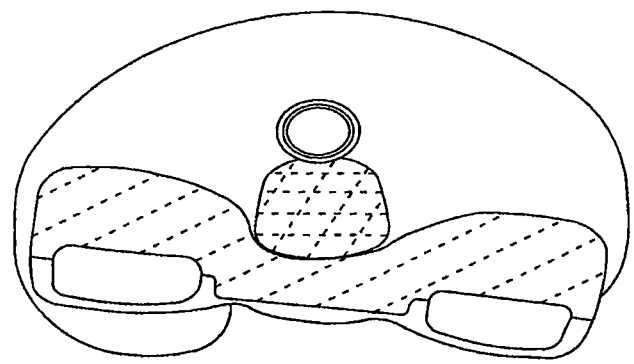
FIG. 12 illustrates a partial cross sectional view from the top down of the prosthesis of the present invention at about 145° flexion.

By way of further illustration, FIGS. 10-12 shows a top-down partial cross sectional view of the prosthesis during flexion of 45°, 90°, and 145°, respectively. As can be seen from these views, the cam has a shape and size quite different on the lateral side than on its medial side. This cam and its particular shape and orientation provides an angled surface which acts with the post to drive a very precise medial pivot and femoral rotation in the transverse plane.

Figure 13:
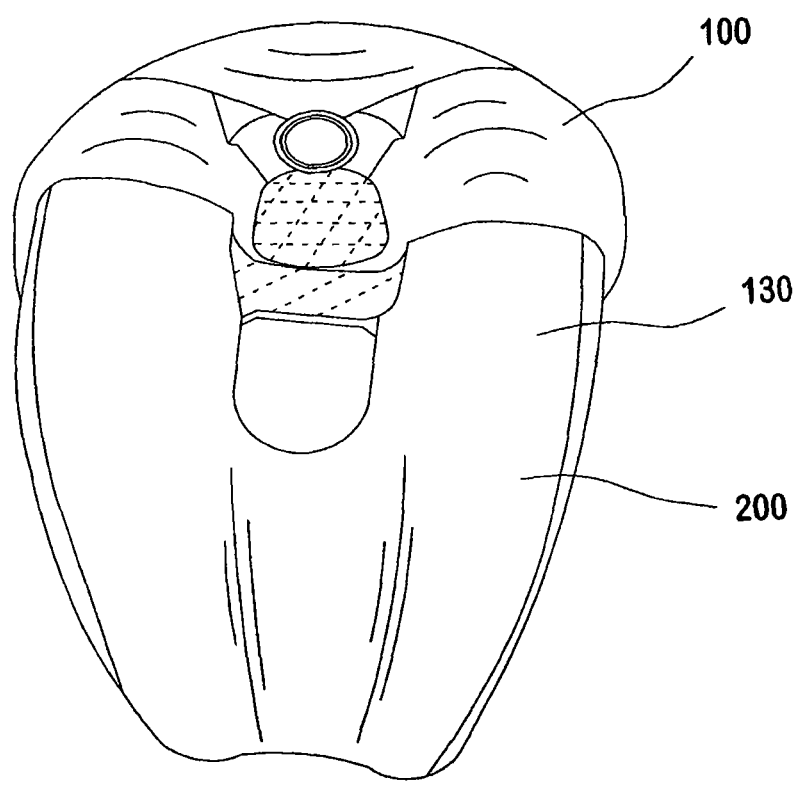
FIG. 13 illustrates a top down view of the prosthesis of the present invention at about 145° flexion.

FIG. 13 illustrates a top down view of the cam and post interaction and also shows the medial rotation of the femoral component with respect to its tibial component. Note that even at this relatively high flexion, the cam is disposed somewhat under the post and enlarges in cross sectional area toward the lateral end of the cam where it abuts the lateral condyle 130.

Figure 14:
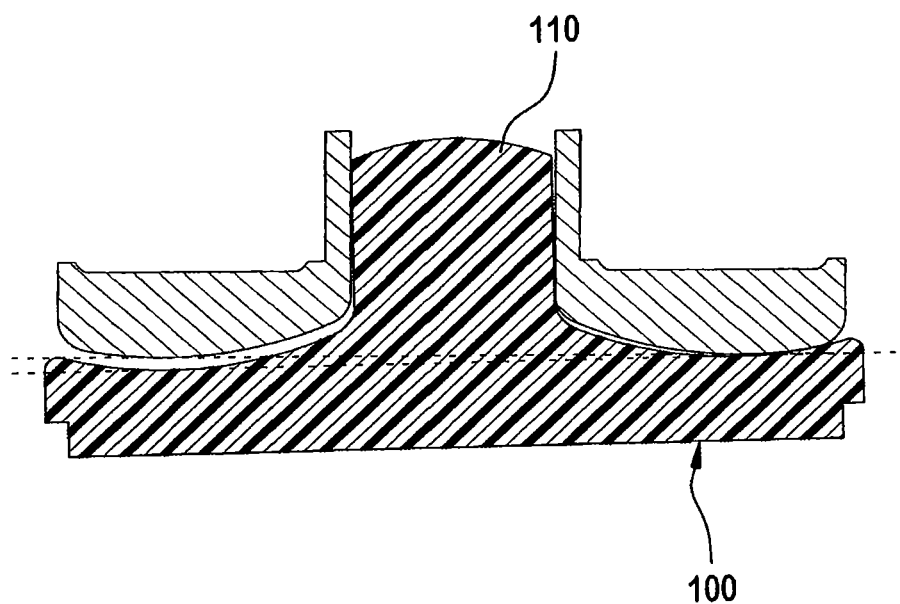
FIG. 14 illustrates a cross sectional view at high flexion showing separation of the lateral condyle from tibial component.
Figure 15:
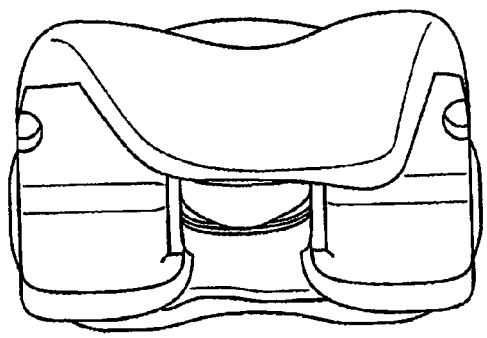
FIG. 15 illustrates the concave curvatures of the medial and lateral surfaces of the cam at a point of post contact at relatively lower flexion.
Figure 16:
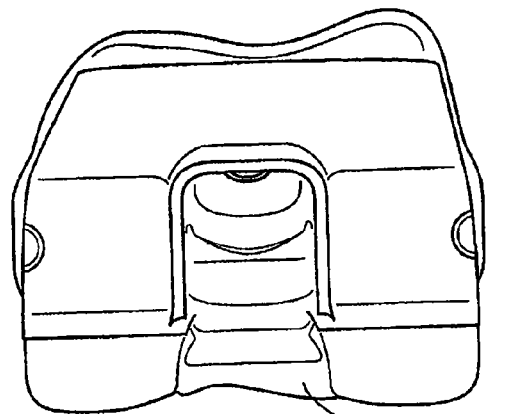
FIG. 16 illustrates the convex curvatures of the medial and lateral surfaces of the cam which will contact the post at a relatively higher flexion.
Figure 17:
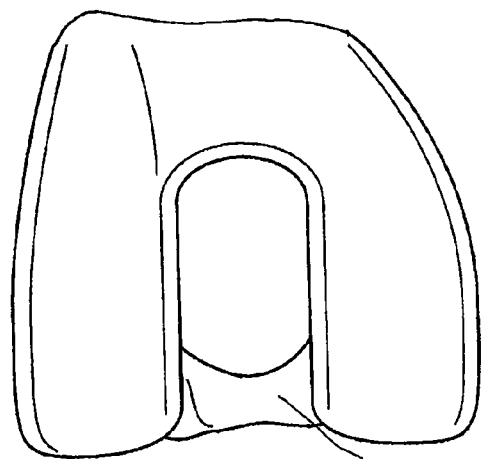
FIG. 17 illustrates the convex and concave surfaces.

It is also noteworthy that the design of the present invention provides for lift-off of the lateral condyle from the tibial load bearing surface at high flexion. See, for example, FIG. 14, which shows separation of the lateral condyle 140 from tibial component 100. This separation is due in part to the architecture of the cam and the post to which it engages during flexion. The separation so achieved aids in replicating anatomically correct movement.

One advantage to the prosthesis of the present invention is that it allows for less soft tissue strain by allowing for more anatomical movement instead of equal rollback in both compartments of the tibial insert. This design gives three advantages over previous designs: 1) less soft tissue strain due to more anatomical movement, 2) better natural motion replication in the medial compartment without increasing constraint, and 3) decreased tibial strain with no edge loading in the medial compartment. Although the above illustrations show knee flexion at 0°, 90°, and 145°, the range of motion allowed for in the design would be at least −10° (hyperextension) to about 160° (high flexion) with supported articulation in the medial and lateral compartments of the knee.

Moreover, as flexion continues beyond 45°, anterior/posterior translation continues to occur, but is guided by the post/asymmetric-cam interaction. Because of the relative dimensions of the post, and in particular the type of asymmetrical cam on the femoral component, proper rotational movement between the femoral component and tibial component is achieved.

Consistent with that described above, the interaction between the tibial component post and the femoral component tapered asymmetric cam, is designed to preferably begin at 45° flexion. It should be noted that the interaction can be controlled through manipulation of the dimensions of the post and cam. This is accomplished through varying the cross-sectional dimensions of the cam from a medial to lateral direction, with the lateral portion of the cam being generally larger than the medial portion. More specifically, the largest cross-sectional area of the cam occurs where the cam meets the lateral condyle. Moving in a medial direction, the cam tapers in a manner consistent with that which causes kinematic rotation as the knee bends past 45° flexion.

It is also noteworthy that there is no interaction between the post and cam at full extension. This prevents unnecessary wear on the tibial post which would otherwise weaken it over time and could even result in failure (i.e., it could shear off).

Figure 18:
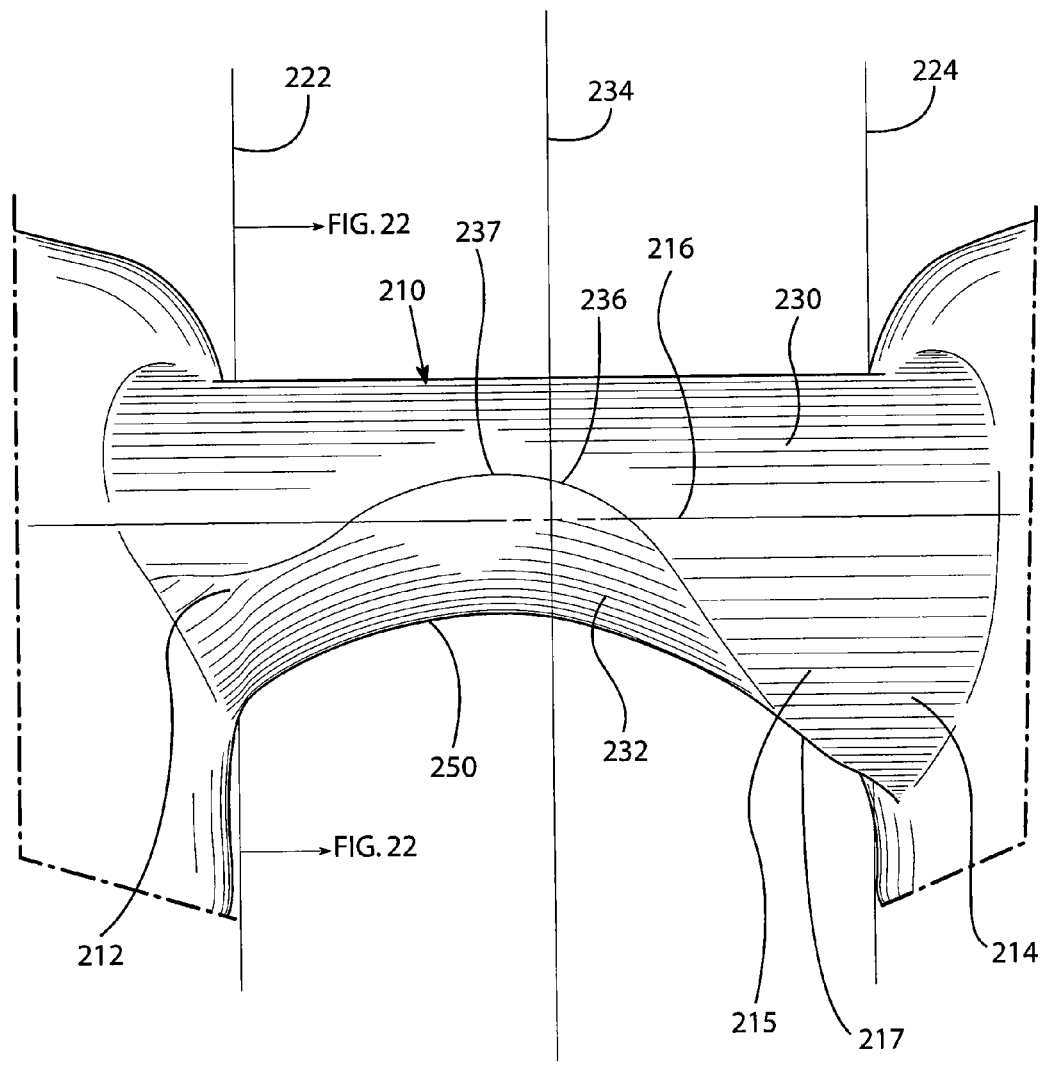
FIG. 18 is an enlarged view of a cam on the femoral component, showing the posterior side of the cam, with other sections of the femoral component truncated for clarity.
Figure 19:
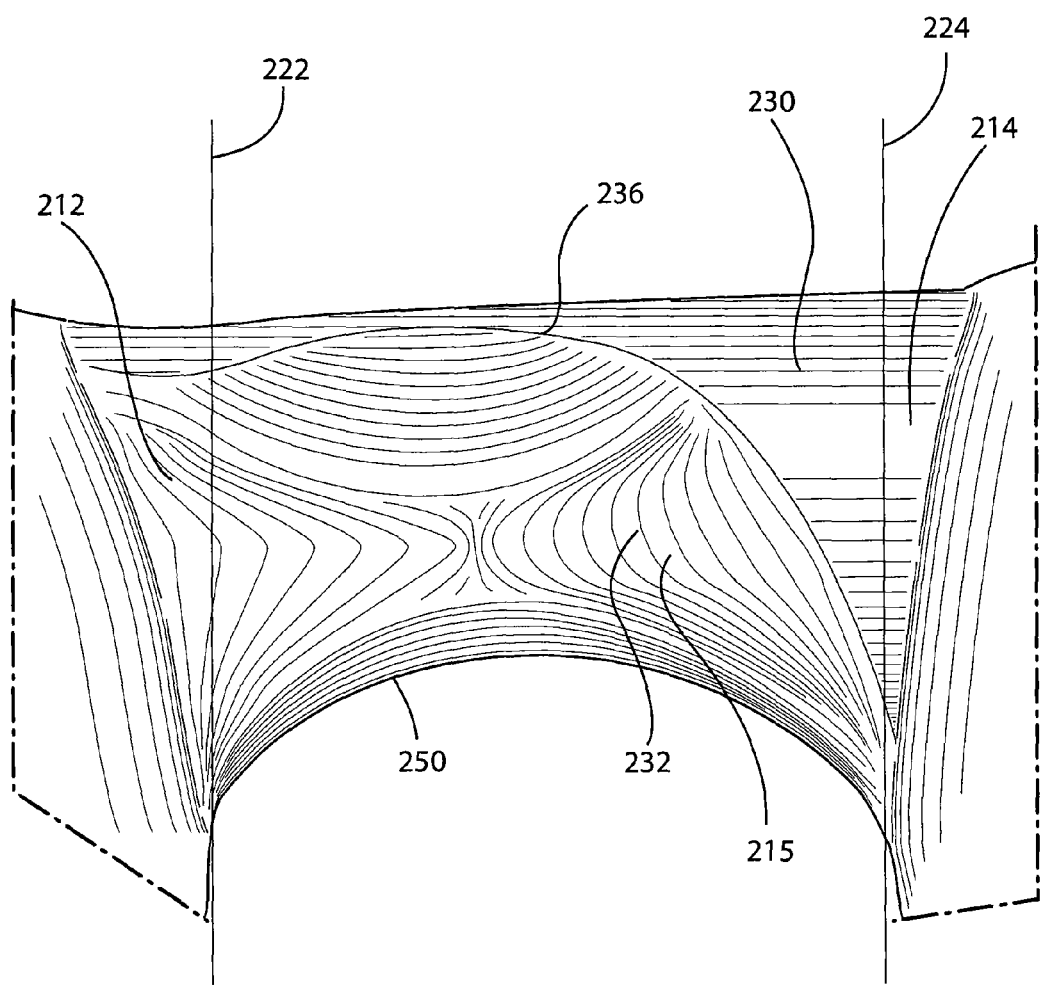
FIG. 19 is an enlarged view of the cam of FIG. 18, showing the bottom or inferior side of the cam, with other sections of the femoral component truncated for clarity.
Figure 20:
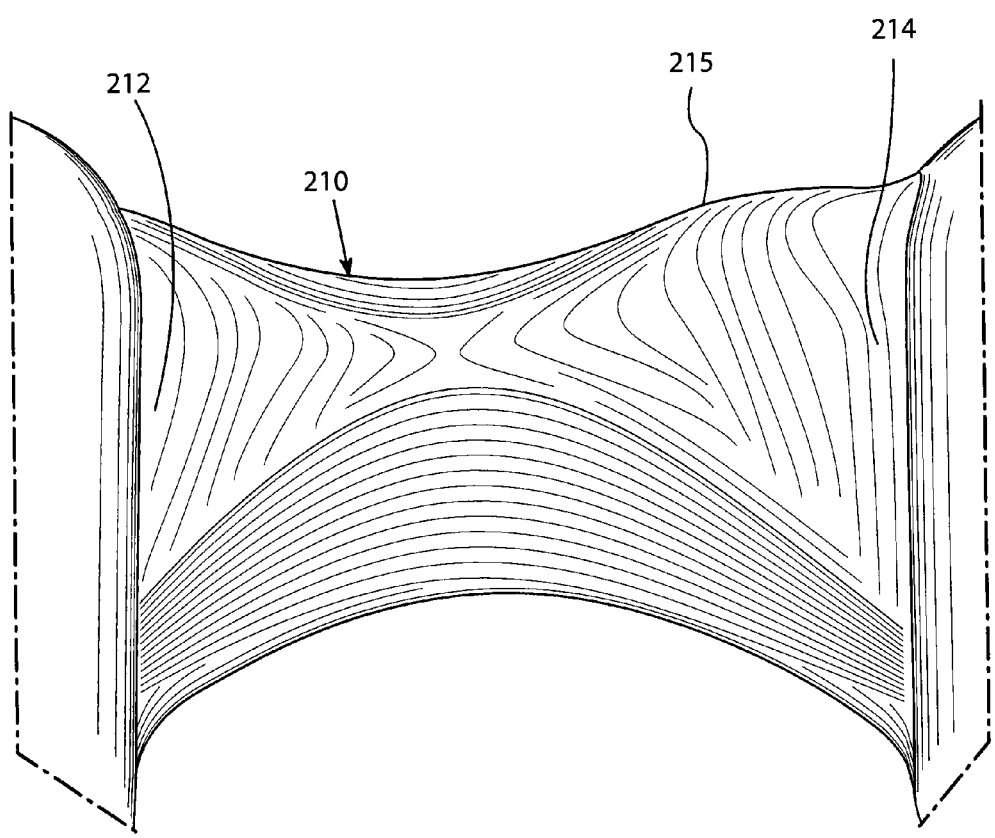
FIG. 20 is an enlarged view of the cam of FIG. 18, showing the anterior side of the cam, with other sections of the femoral component truncated for clarity.
Figure 21:
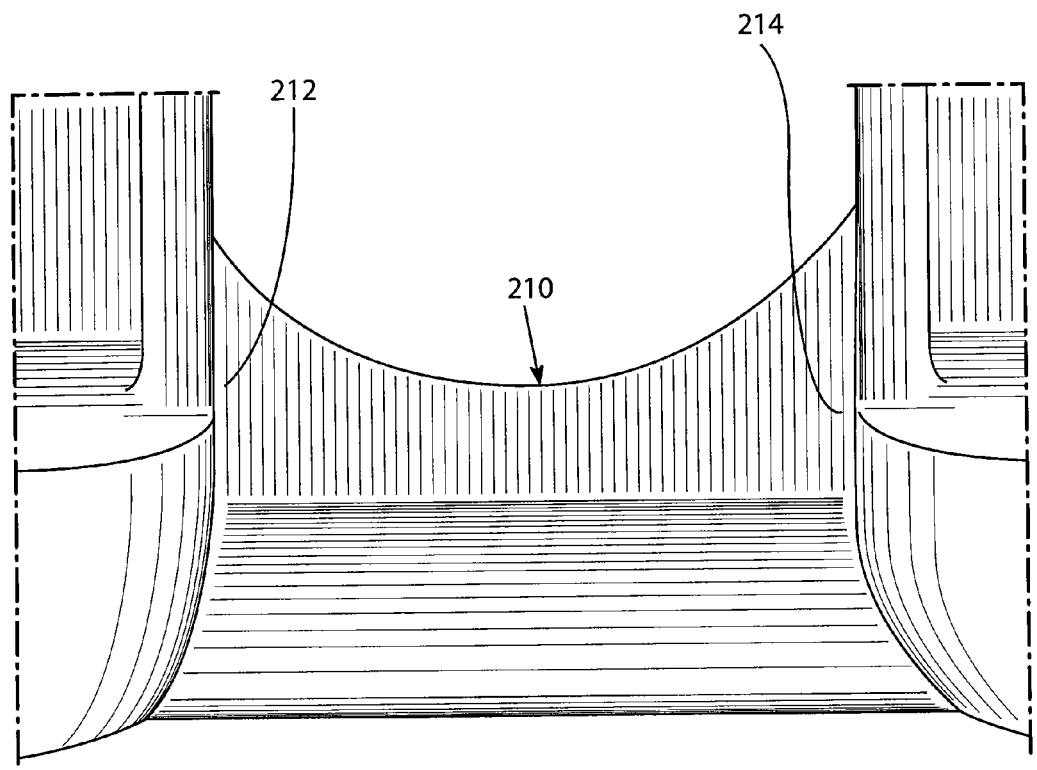
FIG. 21 is an enlarged view of the cam of FIG. 18, showing the top or superior side of the cam, with other sections of the femoral component truncated for clarity.

Cam 210 has a specially contoured architecture that causes medial rotation of the femoral component when the femoral and tibial components move together through a certain range of flexion. This contour can be seen best in FIGS. 2 and 15-21. Referring to FIG. 18, cam 210 includes a medial end 212 in proximity to a medial plane 222, and a lateral end 214 in proximity to a lateral plane 224 that extends parallel to the medial plane. A longitudinal axis 216 extends through cam 210 from the medial end 212 to the lateral end 214. A central plane 234 intersects the midpoint of longitudinal axis 216 and extends parallel to medial plane 222 and lateral plane 224. Central plane 234 is equidistant from medial plane 222 and lateral plane 224.

Cam 210 is asymmetrical with respect to central plane 234. Lateral end 214 has a larger cross-sectional area than medial end 212 of the cam. In addition, cam 210 features a lobe region 215 in proximity to lateral end 214. Lobe region 215 has a convex curvature 217. Cam 210 also features a first surface 230 having a uniform surface contour—that is, a uniform curvature on its surface between medial plane 222 and lateral plane 224—and a second surface 232 having a non-uniform surface contour. The first surface 230 and second surface 232 border one another along a ridgeline 236 that extends between the first and second surfaces. Ridgeline 236 extends from the medial end 212 to the lateral end 214, and follows a U-shaped curve. Second surface 232 includes an irregularly shaped bearing surface 250. As will be described, irregularly shaped bearing surface 250 forms a U-shaped channel that winds around cam 210 from a centered position to a position that is offset toward the medial end of the cam. This shift toward the medial end of the cam causes the medial pivot motion.

Figure 22:
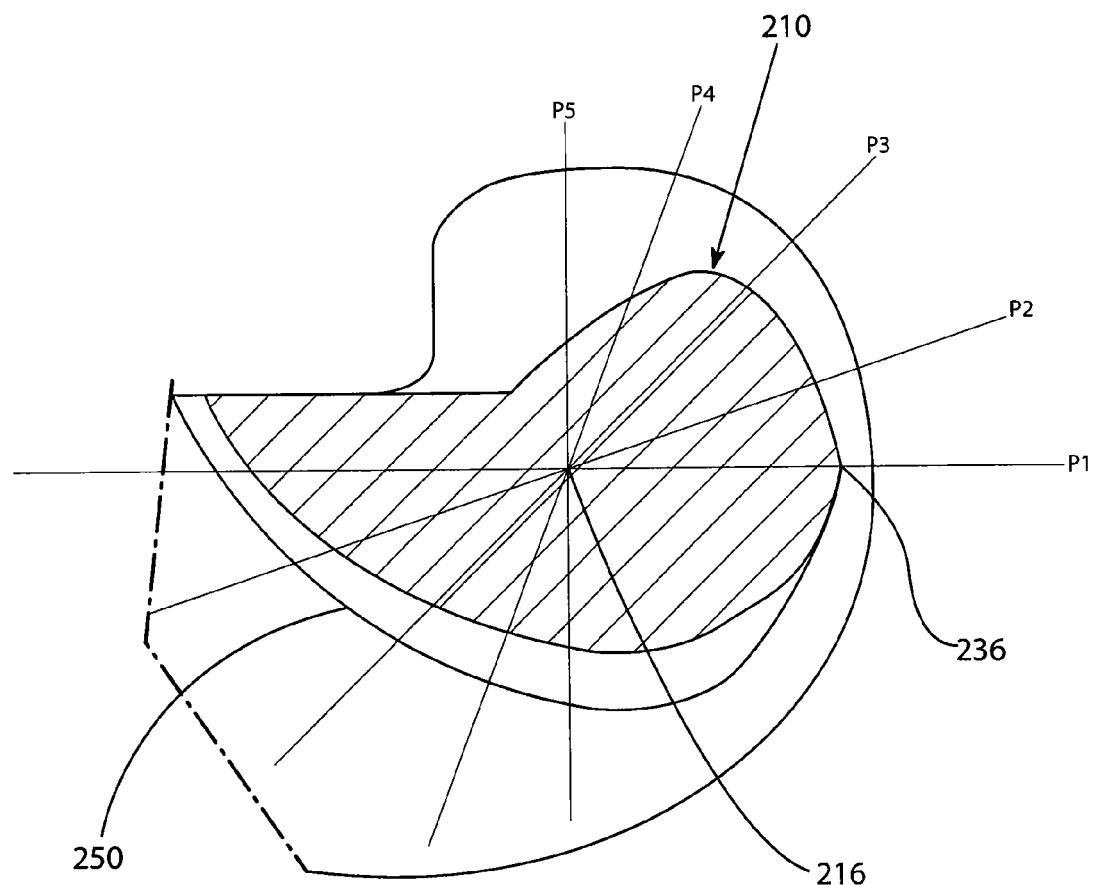
FIG. 22 is a cross-sectional view of the cam of FIG. 18, taken through line 22-22 of FIG. 18.
Figure 23:
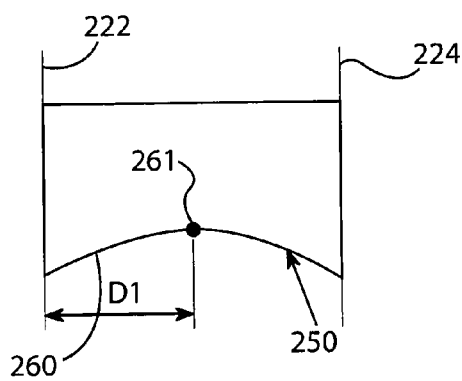
FIG. 23 is a cross-sectional view of the cam of FIG. 18, taken through a first reference plane P1 in FIG. 22.
Figure 24:
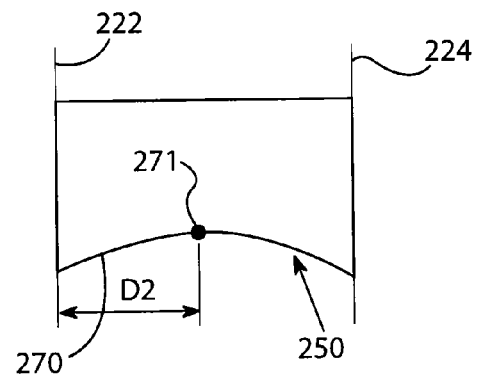
FIG. 24 is a cross-sectional view of the cam of FIG. 18, taken through a second reference plane P2 in FIG. 22.
Figure 25:
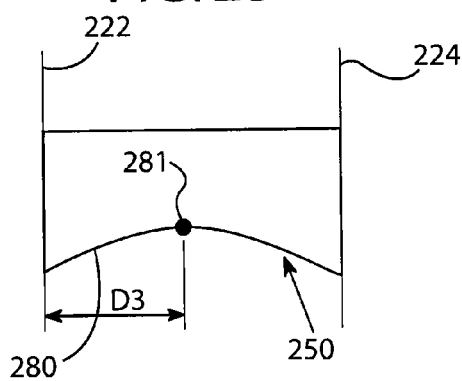
FIG. 25 is a cross-sectional view of the cam of FIG. 18, taken through a third reference plane P3 in FIG. 22.
Figure 26:
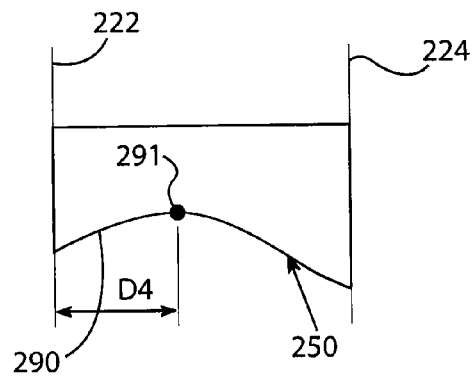
FIG. 26 is a cross-sectional view of the cam of FIG. 18, taken through a fourth reference plane P4 in FIG. 22.
Figure 27:
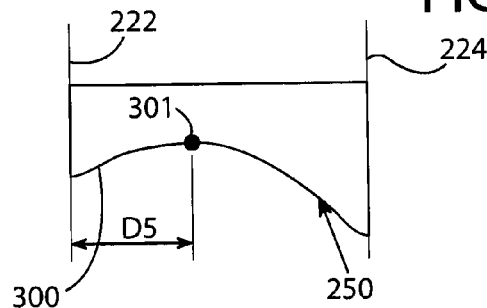
FIG. 27 is a cross-sectional view of the cam of FIG. 18, taken through a fifth reference plane P5 in FIG. 22.
Figures 28, 29:
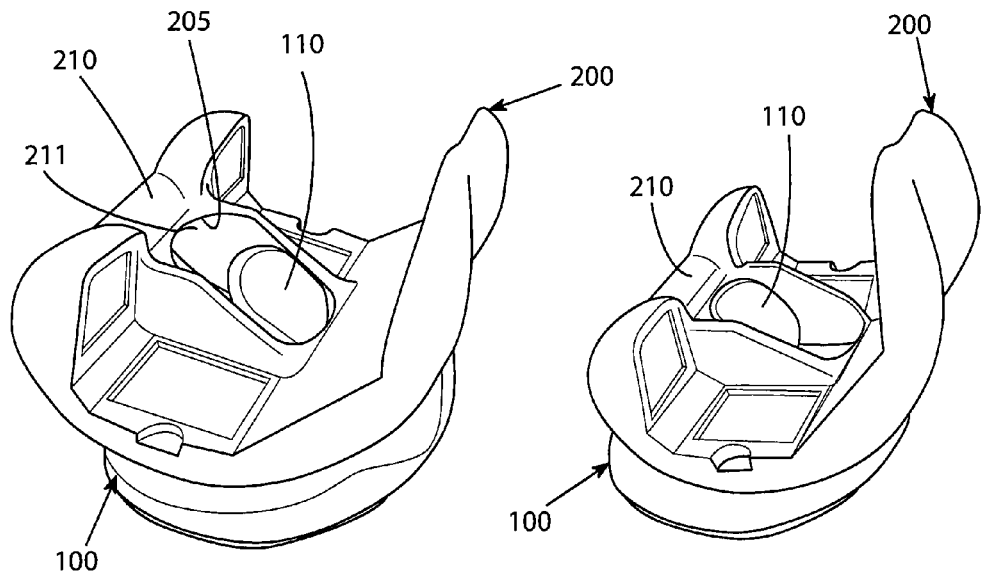
FIG. 28 is a perspective view of a femoral component cooperatively engaged with a tibial component in accordance with the invention, shown in a position of no flexion.
FIG. 29 is another perspective view of a femoral component cooperatively engaged with a tibial component in accordance with the invention, shown in a position of flexion.
Figures 30, 31:
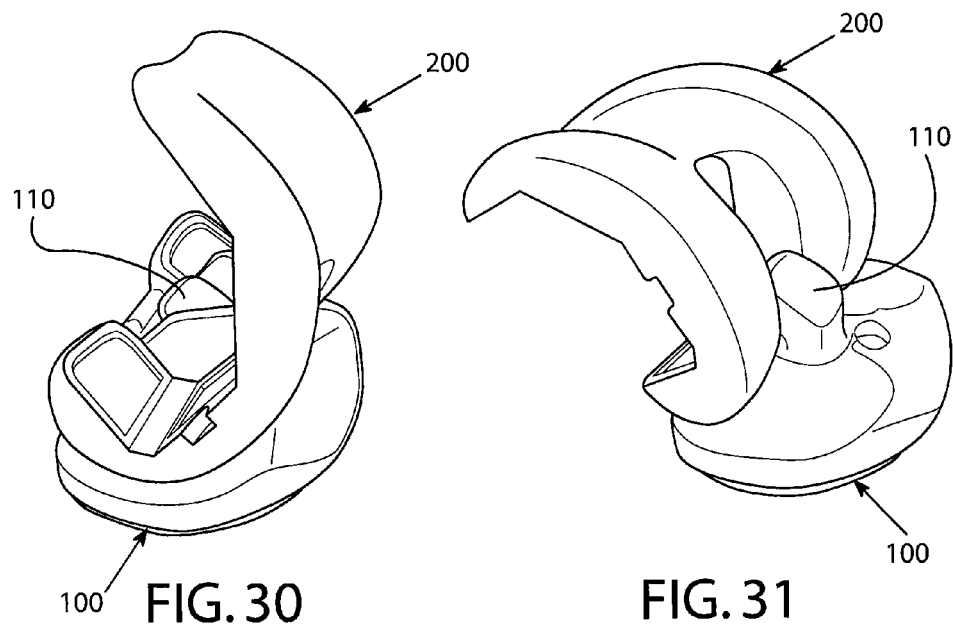
FIG. 30 is another perspective view of a femoral component cooperatively engaged with a tibial component in accordance with the invention, shown in a position of further flexion.
FIG. 31 is another perspective view of a femoral component cooperatively engaged with a tibial component in accordance with the invention, shown in a position of further flexion.
Figure 32:
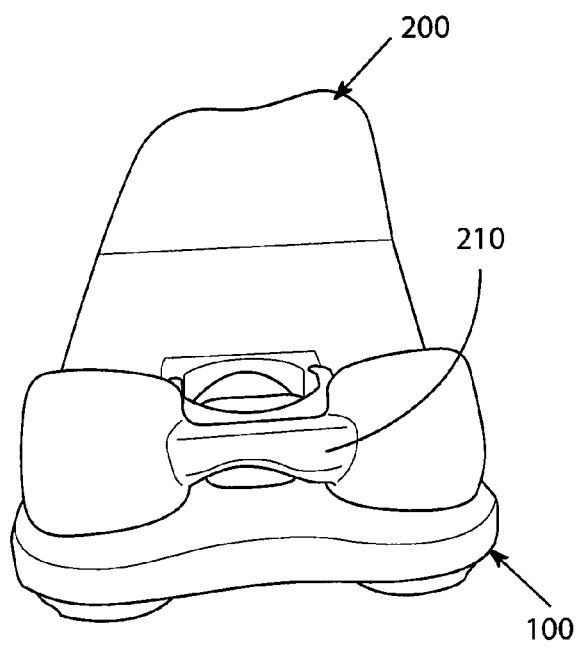
FIG. 32 is another perspective view of a femoral component cooperatively engaged with a tibial component in accordance with the invention.
Figure 33:
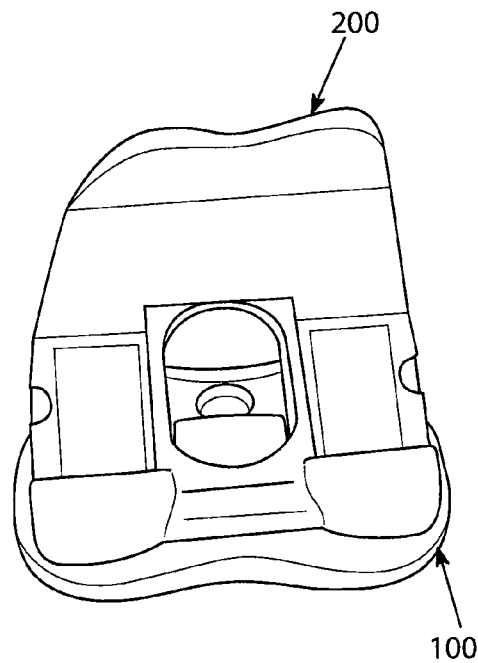
FIG. 33 is another perspective view of a femoral component cooperatively engaged with a tibial component in accordance with the invention.
Figure 34:
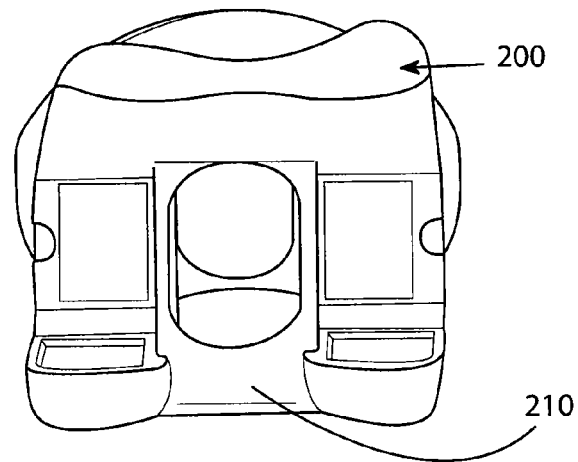
FIG. 34 is another perspective view of a femoral component cooperatively engaged with a tibial component in accordance with the invention.

Referring to FIG. 22, bearing surface 250 is shown in further detail. Bearing surface 250 has a variable curvature that can be visualized by viewing cross-sectional profiles of cam 210 between medial plane 222 and lateral plane 224. For this purpose, FIG. 22 shows five different planes of reference, P1, P2, P3, P4 and P5, that extend through the longitudinal axis 216 of cam 210. Planes P1-P5 extend through an angle of 90 degrees, with plane P1 perpendicular to plane P5. In addition, planes P1-P5 extend perpendicularly with respect to central plane 234. Planes P1-P5 intersect bearing surface 250 along five different curvatures extending between medial plane 222 and lateral plane 224. The five curvatures are shown in FIGS. 23-27.

A first curvature 260 is defined by plane P1, a second curvature 270 is defined by plane P2, a third curvature 280 is defined by plane P3, a fourth curvature 290 is defined by plane P4, and a fifth curvature 300 is defined by plane P5. Each of the curvatures has a vertex. The term "vertex", as used herein, refers to the point on the curve where the first derivative of curvature is zero, as for example, the vertex on a parabola. First curvature 260 is a concave curve with a vertex 261, second curvature 270 is a concave curve with a vertex 271, third curvature 280 is a concave curve with a vertex 281, fourth curvature 290 is a concave curve with a vertex 291 and fifth curvature 300 is a concave curve with a vertex 301.

Proceeding from plane P1 to plane P5, the shape of bearing surface 250 gradually transitions from a curve with a vertex that is centered between the medial plane 222 and lateral plane 224, to a curve with a vertex that is off-centered with respect to the medial and lateral planes. In addition, the curvature of bearing surface 250 transitions from a curve that is symmetrical with respect to the central plane 234, to a curve that is asymmetrical with respect to the central plane. The distance between the medial plane 222 and the vertex of each curvature gradually decreases from plane P1 to plane P5. That is, the distance D2 between medial plane 222 and vertex 271 in plane P2 is less than the distance D1 between the medial plane and vertex 261 in plane P1. Similarly, the distance D3 between medial plane 222 and vertex 281 in plane P3 is less than the distance D2 between the medial plane and vertex 271 in plane P2, and so forth. In plane P1, the distance D1 between vertex 261 and medial plane 222 is equal to the distance between vertex 261 and lateral plane 224. In plane P5, however, the distance D5 between vertex 301 and medial plane 222 is significantly less than the distance between vertex 301 and lateral plane 224. The vertices defined in planes P1 and P5, and every plane in between, gradually shift from a position that is centered between the medial plane 222 and lateral plane 224, to a position that is more and more offset toward the medial plane.

When the femoral and tibial components move through certain angles of flexion, post 110 engages each curvature on the cam 210 in close proximity to the vertex of each curvature. As the femoral and tibial components move from a lower angle of flexion to a higher angle of flexion, the contact area between the post 110 and cam 210 gradually shifts toward the medial end 212 of the cam in response to the gradual change in position of the vertices toward the medial end. This causes the femoral component to pivot relative to the post, resulting in a medial pivot motion.

The U-shaped curve of ridgeline 236 also has a vertex 237. The distance between vertex 237 of ridgeline 236 and lateral plane 224 is greater than the distance between the vertex of the ridgeline and medial plane 222.

FIGS. 28-34 provide additional views of femoral component 200 and tibial component 100 engaged with one another in various degrees of flexion.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the scope of the invention.

What is claimed:

1. A knee prosthesis comprising:
   a femoral component having two condyles with an opening disposed between the two condyles, and an asymmetrical cam extending between the condyles, the cam having a medial end generally conforming to a medial plane, and a lateral end generally conforming to a lateral plane, the lateral plane extending generally parallel to the medial plane, the cam having a longitudinal axis extending from the medial end to the lateral end perpendicularly to the medial and lateral planes, and a central plane that extends substantially parallel to the medial plane and lateral plane, the central plane being substantially equidistant from the medial plane and lateral plane; and
   a tibial component having bearing surfaces to support each of the femoral component condyles, and a post disposed between the bearing surfaces and extending superiorly from the tibial component;
   the femoral component and tibial component engageable by contact between the femoral condyles and tibial bearing surfaces, and by contact between the cam and post during at least a portion of flexion between the femoral and tibial components;
   the cam comprising a first curvature defined by a first plane passing through the cam, and a second curvature defined by a second plane passing through the cam, the first and second planes each extending parallel to the longitudinal axis and perpendicular to the central plane,
   the cam and post configured so that the first curvature on the cam contacts the post at a lower degree of flexion, and the second curvature on the cam contacts the post at a higher degree of flexion,
   the first curvature comprising a concave curve having a first vertex, and the second curvature comprising a concave curve having a second vertex, the distance between the medial plane and the first vertex being greater than the distance between the medial plane and the second vertex, such that moving the femoral and tibial components in flexion from the lower degree of flexion to the higher degree of flexion causes the femoral component to rotate about the post.

2. The knee prosthesis of claim 1, wherein the concave curve of the first curvature is substantially symmetrical with respect to the central plane, and the concave curve of the second curvature is asymmetrical with respect to the central plane.

3. The knee prosthesis of claim 1, wherein the cam comprises a plurality of curvatures between the first and second curvatures, each of the plurality of curvatures comprising a concave curve with a vertex, the distance between each vertex and the medial plane gradually decreasing from the first curvature to the second curvature.

4. The knee prosthesis of claim 1, wherein the cam forms a posterior boundary of the opening.

5. The knee prosthesis of claim 4, wherein the posterior boundary forms a U-shaped curve that is symmetrical with respect to the central plane.

6. The knee prosthesis of claim 5, wherein the post comprises an inclined contact surface.

7. The knee prosthesis of claim 6, wherein the inclined contact surface comprises a U-shaped curvature that mates with the U-shaped curve of the posterior boundary of the opening during at least a portion of flexion between the femoral and tibial components.

8. The knee prosthesis of claim 1, wherein the lateral end of the cam has a larger cross-sectional area than the medial end of the cam.

9. The knee prosthesis of claim 1, wherein the lower degree of flexion comprises a flexion of about 45° and the higher degree of flexion comprises a flexion of about 145°.

10. The knee prosthesis of claim 1, wherein the lateral end of the cam comprises a lobe region having a convex curvature.

11. The knee prosthesis of claim 1, wherein the cam comprises a first surface between the medial and lateral ends having a uniform contour and a second surface between the medial and lateral ends having a non-uniform contour, the first and second surfaces bordering one another along a ridgeline that extends between the first and second surfaces.

12. The knee prosthesis of claim 11, wherein the ridgeline extends from the medial end to the lateral end.

13. The knee prosthesis of claim 11, wherein the ridgeline follows a U-shaped curve between the medial end and the lateral end.

14. The knee prosthesis of claim 13, wherein the U-shaped curve of the ridgeline has a vertex, the distance between the vertex of the ridgeline and the lateral plane being greater than the distance between the vertex and the medial plane.

* * * * *